United States Patent
Yoshida

(10) Patent No.: US 8,968,754 B2
(45) Date of Patent: Mar. 3, 2015

(54) TITANIUM DIOXIDE DISPERSION AND COSMETICS CONTAINING THE SAME

(75) Inventor: Susumu Yoshida, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 381 days.

(21) Appl. No.: 13/056,682

(22) PCT Filed: Dec. 14, 2009

(86) PCT No.: PCT/JP2009/006848
§ 371 (c)(1),
(2), (4) Date: Jan. 31, 2011

(87) PCT Pub. No.: WO2010/070867
PCT Pub. Date: Jun. 24, 2010

(65) Prior Publication Data
US 2011/0129509 A1   Jun. 2, 2011

(30) Foreign Application Priority Data
Dec. 18, 2008   (JP) .................... 2008-321996

(51) Int. Cl.
| A61K 8/02 | (2006.01) |
| A01N 25/26 | (2006.01) |
| A01N 25/28 | (2006.01) |
| A01N 59/16 | (2006.01) |
| A61K 33/24 | (2006.01) |
| C09C 1/36 | (2006.01) |
| A61K 8/06 | (2006.01) |
| A61K 8/11 | (2006.01) |
| A61K 8/29 | (2006.01) |
| A61K 8/37 | (2006.01) |
| A61K 8/894 | (2006.01) |
| A61Q 17/04 | (2006.01) |
| A61Q 19/00 | (2006.01) |

(52) U.S. Cl.
CPC ............... *C09C 1/3692* (2013.01); *A61K 8/062* (2013.01); *A61K 8/11* (2013.01); *A61K 8/29* (2013.01); *A61K 8/37* (2013.01); *A61K 8/894* (2013.01); *A61Q 17/04* (2013.01); *A61Q 19/00* (2013.01); *C09C 1/3661* (2013.01); *C09C 1/3669* (2013.01); *C09C 1/3676* (2013.01); *C09C 1/3684* (2013.01); *A61K 2800/412* (2013.01)
USPC ............... 424/401; 424/421; 424/617

(58) Field of Classification Search
USPC ................... 424/497, 401, 421, 617
See application file for complete search history.

(56) References Cited

U.S. PATENT DOCUMENTS

| 5,468,471 A | 11/1995 | Zecchino et al. |
| 2004/0091440 A1 | 5/2004 | Kamei et al. |
| 2004/0146472 A1 * | 7/2004 | Nakanishi .................. 424/70.12 |
| 2007/0253989 A1 * | 11/2007 | Abe et al. ...................... 424/401 |
| 2009/0081142 A1 | 3/2009 | Omura et al. |
| 2009/0252774 A1 | 10/2009 | Kamei et al. |
| 2011/0250248 A1 | 10/2011 | Omura et al. |

FOREIGN PATENT DOCUMENTS

| CN | 101312706 A | 11/2008 |
| EP | 1772138 A2 | 4/2007 |
| EP | 1955691 A1 | 8/2008 |
| EP | 2107080 A1 | 10/2009 |
| JP | 59-172415 | 9/1984 |
| JP | 1-57084 | 12/1989 |
| JP | 2000-128775 | 5/2000 |
| JP | 2000-169353 | 6/2000 |
| JP | 2000-264824 | 9/2000 |
| JP | 2004-155978 | 6/2004 |
| JP | 2007-84475 | 4/2007 |
| JP | 2009-263213 | 11/2009 |
| WO | WO2006/100018 | * 9/2006 |
| WO | 2007/060823 | 5/2007 |

OTHER PUBLICATIONS

Japanese Patent Abstract for Publication No. 2000-169353 Published Jun. 20, 2000, 14 pages.
Japanese Patent Abstract for Publication No. 2000-264824 Published Sep. 26, 2000, 10 pages.
Japanese Patent Abstract for Publication No. 2007-084475 Published Apr. 5, 2007, 20 pages.
Japanese Patent Abstract for Publication No. 58-049307 Published Mar. 23, 1983, 1 page.
Japanese Patent Abstract for Publication No. 59-172415 Published Sep. 29, 1984, 1 page.
International Search Report for corresponding PCT /JP2009/006848 mailed Mar. 16, 2010, 2 pages.
International Preliminary Report on Patentability (Translation) issued Jul. 5, 2011 for corresponding International Application No. PCT/JP2009/006848, filed Dec. 14, 2009, Applicant: Shiseido Company Ltd., 7 Pages.
European Search Report, Application No. 09833175.4, dated Apr. 11, 2012, six pages.

* cited by examiner

*Primary Examiner* — Benjamin Packard
(74) *Attorney, Agent, or Firm* — Rankin, Hill & Clark LLP

(57) ABSTRACT

The present invention provides a titanium dioxide dispersion having a good dispersibility and also provides a cosmetic containing the same. The titanium dioxide dispersion comprises (a) a hydrophobized, treated titanium dioxide powder; (b) one or more oils selected from isohexadecane, isododecane, 2-ethylhexyl 2-ethylhexanoate, isononyl isononate, 2-ethylhexyl isononanoate, isononyl 2-ethylhexanoate, and polypropylene glycol dipivalate; and (c) a siloxane compound represented by the following formula (1), preferably polyoxyalkylene/alkyl comodified organopolysiloxane.

$$R^1_a R^2_b R^3_c SiO_{(4-a-b-c)/2} \qquad (1)$$

16 Claims, No Drawings

TITANIUM DIOXIDE DISPERSION AND COSMETICS CONTAINING THE SAME

FIELD OF THE INVENTION

The present invention relates to a titanium dioxide dispersion, and in particular, relates to a titanium dioxide dispersion having an excellent dispersibility and to cosmetics incorporating the same.

BACKGROUND OF THE INVENTION

For outdoor leisure or sports, sunscreen creams and the like have been used for some time to prevent the skin from being exposed to excessive UV and causing inflammation.

Recently, it became known that the UV, to which we are unconsciously exposed on a daily basis, contributes to developing pigmented spots and freckles, wrinkles owing to photo aging, and skin cancers owing to gene damage of skin cells. Hence, specialists such as dermatologists recommend protecting the skin from UV on a daily basis.

Following to such trend, most cosmetics such as a lotion, a milky lotion, a cream, and a foundation are now provided with UV protection abilities. The substances having UV protection ability include organic substances as UV absorbers and inorganic substances as UV scatterers, and the inorganic substances which are considered to have higher safety are relatively preferred.

For the inorganic substances as UV scatterers, titanium dioxide is most often used. Titanium dioxide has the largest refractive index (2.3 to 2.6) in pigments and also has the largest hiding power in white pigments. However, there has been a problem that it was difficult to disperse titanium dioxide on its own in a cosmetic base.

As the techniques for improving the dispersibility of titanium dioxide in cosmetics, the one that the surface of particulate titanium dioxide is coated with metallic soap (e.g., Patent Literatures 1 and 2) and the one that the surface of particulate metal oxide is coated with silane compound (e.g., Patent Literature 3) are known.

These sunscreen cosmetics in which titanium dioxide is used as UV protection agent are generally prepared by incorporating the titanium dioxide treated with fatty acid soap, cyclic silicones such as decamethylcyclopentasiloxane, and silicone-based dispersant aids.

However, these cosmetics could not have a sufficient dispersibility of titanium dioxide even with using such methods, they provided stickiness peculiar to the dispersant aids because of a lot of dispersant aid needed for dispersing, and they had limitations for improving the UV protection ability while increasing the powder concentration of titanium dioxide.

So, an organic dispersion, in which titanium dioxide is dispersed in an organic compound having branched chains without using dispersant aids, has been developed (Patent Literature 4). However, this organic dispersion had a problem of a poor feeling in use.

Patent Literature 1: Japanese Examined Patent Publication No. H1-57084
Patent Literature 2: Japanese Unexamined Patent Publication No. S59-172415
Patent Literature 3: Japanese Unexamined Patent Publication No. 2000-264824
Patent Literature 4: Japanese Unexamined Patent Publication No. 2000-128755

DISCLOSURE OF THE INVENTION

Problem to be Solved by the Invention

The object of the present invention is to provide a titanium dioxide dispersion having a good dispersibility by using a small amount of dispersant and to provide a stable cosmetic containing the same which provides a good feeling in use.

Means to Solve the Problem

As a result that the present inventors have diligently studied, they found that a titanium dioxide dispersion in which a modified titanium dioxide is well dispersed can be obtained by combining specific dispersant and oil.

The present invention provides a titanium dioxide dispersion comprising the following (a) to (c):

(a) a hydrophobized, treated titanium dioxide powder;
(b) one or more oils selected from isohexadecane, isododecane, 2-ethylhexyl 2-ethylhexanoate, isononyl isononate, 2-ethylhexyl isononanoate, isononyl 2-ethylhexanoate, and polypropylene glycol dipivalate; and
(c) a siloxane compound represented by the following formula (1):

wherein $R^1$s are identical or different organic groups in which at least one or more alkyl groups having 10 or more carbon atoms are contained as essential components, and $R^1$s are selected from the organic groups having 1 to 18 carbon atoms such as an alkyl group, an aryl group, an aralkyl group, a fluorine-substituted alkyl group, an amino-substituted alkyl group, a carboxy-substituted alkyl group, and an organic group represented by the following formula (2):

$$—C_mH_{2m}—O—(C_2H_4O)_d(C_3H_6O)_e—R^4 \quad (2)$$

$R^2$s are identical or different organic groups selected from an organic group having a polyoxyalkylene group represented by the following formula (3) and an organic group represented by the following formula (4) wherein Q represents a divalent hydrocarbon group having 3 to 20 carbon atoms which may have at least one of an ether bond and an ester bond, and X represents a polyhydric alcohol-substituted hydrocarbon group having at least two hydroxyl groups;

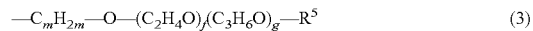

$R^3$ is organopolysiloxane represented by the following formula (5); $R^4$ is a hydrocarbon group having 4 to 30 carbon atoms or an organic group represented by $R^6—(CO)—$; $R^5$ is a hydrogen atom, a hydrocarbon group having 1 to 30 carbon atoms, or an organic group represented by $R^6—(CO)—$; $R^6$ is a hydrocarbon group having 1 to 30 carbon atoms;

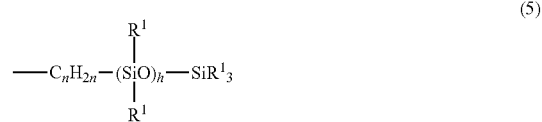

d and e are respectively any integer of $0 \le d \le 50$ and $0 \le e \le 50$; f and g are respectively any integer of $2 \le f \le 200$ and $0 \le g \le 200$, and f+g is 3 to 200; h is any integer of $1 \le h \le 500$; m and n are respectively any integer of $0 \le m \le 15$ and $1 \le n \le 5$; and a, b, and c are respectively any integer of $1.0 \le a \le 2.5$, $0.001 \le b \le 1.5$, and $0.001 \le c \le 1.5$.

Also, the present invention provides a cosmetic comprising the above-mentioned titanium dioxide dispersion.

Effect of the Invention

BRIEF DESCRIPTION OF THE DRAWINGS

The titanium dioxide dispersion of the present invention is highly excellent in dispersibility in oils and dispersion stability with use of a small amount of dispersant.

The cosmetic of the present invention provides an excellent UV protection ability, an excellent dispersibility of powder, and a good feeling in use owing to the incorporation of the titanium dioxide dispersion of the present invention. Since the cosmetic can maintain a stable dispersibility with use of a small amount of dispersant, it can be free from stickiness and provide a good feeling in use. Moreover, even when oil-soluble UV absorbers are incorporated together with the titanium dioxide dispersion, the UV absorbers hardly precipitate under a long-term storage, thus achieving a high stability.

BEST MODE FOR CARRYING OUT THE INVENTION

Hereinafter, the best mode for carrying out the present invention will be described.

In the present invention, the titanium dioxide dispersion having a good dispersibility with use of a small amount of dispersant can be achieved by using the after-mentioned specific dispersant in combination with specific oil.

The hydrophobized, treated titanium dioxide powder (a) of the present invention is described below.

Hydrophobizing agents for the treated titanium dioxide powder (a) is not limited in particular, and any publicly known hydrophobizing agents can be generally used. Specific examples of the hydrophobizing agents include silicone compounds such as dimethylpolysiloxane, methylhydrogenpolysiloxane, and methylphenylpolysiloxane; fluorine compounds such as perfluoroalkyl group-containing ester, perfluoropolyether, and perfluoroalkyl group-containing polymer; oil agents such as liquid paraffin, squalane, petrolatum, lanolin, microcrystalline wax, and polyethylene wax; metallic soaps such as aluminum laurate and aluminum stearate; organic titanates such as isopropyltriisostearoyl titanate; and silane coupling agents such as perfluoroalkyl silane and octyltriethoxysilane. One or more of them can be used.

For a titanium dioxide used for the hydrophobized, treated titanium dioxide powder (a) used in the present invention, a titanium dioxide coated with silica or alumina is preferably used, and the examples include hydrophobized, treated titanium dioxide powder wherein a silica-coated titanium dioxide is hydrophobized with a silane coupling agent and a cationic surfactant (e.g., titanium dioxide OTQ-MT-100Si, manufactured by Tayca Corporation), hydrophobized, treated titanium dioxide powder wherein silica-coated titanium dioxide is hydrophobized with a silane coupling agent, hydrophobized, treated titanium dioxide powder wherein alumina-coated titanium dioxide is hydrophobized with a higher fatty acid (e.g., titanium dioxide TTO-S-4, manufactured by Ishihara Sangyo Kaisha, LTD.), and hydrophobized, treated titanium dioxide powder wherein silica- and alumina-coated titanium dioxide is hydrophobized with a higher fatty acid and an alkylsilane.

In the present invention, among them, the hydrophobized, treated titanium dioxide powder wherein silica-coated titanium dioxide is hydrophobized with a silane coupling agent and a cationic surfactant is particularly preferred.

Hereinafter, the treated titanium dioxide powder wherein silica-coated titanium dioxide is hydrophobized with a silane coupling agent and a cationic surfactant (a1) will be described.

The silica-coated titanium dioxide as base powder can be prepared by adding sodium silicate to a titanium dioxide slurry.

The silica-coated titanium dioxide of the present invention is not limited in its shape, particle size, or particle structure in particular, and it can take any shape (e.g., sphere, plate, or needle), any particle size (e.g., aerosol size, fine particle, or pigment size), and any particle structure (e.g., porous or nonporous).

The treated titanium dioxide powder (a1) is prepared by treating the above-mentioned silica-coated titanium dioxide with a silane coupling agent and a cationic surfactant.

Examples of the silane coupling agent include perfluoroalkyl silane and octyltriethoxysilane, and octyltriethoxysilane is particularly preferred.

Examples of the cationic surfactant include stearyltrimethylammonium chloride, hexadecyltrimethylammonium chloride, tetradecyltrimethylammonium chloride, lauryltrimethylammonium chloride, C12 monohydroxyalkylether cation, dihydroxyalkylether cation, cocodiamidopropyl cation, cocodicarboxyethyl cation, C16 dicarboxyethyl cation, C18 dicarboxyethyl cation, POP(15) diethylmethyl cation, POP (25) diethylmethyl cation, POP(40) diethylmethyl cation, C12 diamidopropylmethylamine, C14 diamidopropylmethylamine, C16 diamidopropylmethylamine, C18 diamidopropylmethylamine, iso C18 diamidopropylmethylamine, di C18 propyldimethyl cation, hydroxypropyl-bis-lauryl cation, hydroxypropyl-bis-stearyl cation, hydroxypropyl-bis-laurylamide cation, hydroxypropyl-bis-stearylamide cation, C18 monohydroxyalkylether cation, bis-C18 hydroxyalkylether cation, C22 trimethylammonium bromide, C22 propyldimethylamine, quaternium-91, C22 trimethylammonium methosulfate, dicocoylamidoethylethylhydroxy cation, di C18 amidoethylethylhydroxy cation, di C16 amidoethylethylhydroxy cation, di C18 dimethylammonium salt, C18 dimethylbenzylammonium salt, perfluorotrimethylammonium salt, and diacylamidoethylethylhydroxy cation. One or more of them can be used.

Particularly preferable cationic surfactant is distearyldimethylammonium chloride.

It is preferred that the coating amounts of the silane coupling agent and the cationic surfactant are respectively 3 to 90% by mass and 0.5 to 10% by mass with respect to the own weight of the silica-coated titanium dioxide.

It is also preferred that the mass ratio of the coating amounts of the silane coupling agent to the cationic surfactant is 1:1 to 9:1. When the percentage of the cationic surfactant is higher than the above-mentioned range, the water resistance may become worse. When it is lower than the above-mentioned range, the cleansability may become worse.

The following methods are examples for production method of the treated titanium dioxide powder wherein silica-coated titanium dioxide is hydrophobized with a silane coupling agent and a cationic surfactant; however, the present invention is not limited by these examples.

Into a solvent, 3 to 90% by mass of silane coupling agent and 0.5 to 10% by mass of cationic surfactant with respect to the amount of silica-coated titanium dioxide are added and dissolved. Then, the silica-coated titanium dioxide is added therein, and the mixture is stirred for 1 hour at room temperature. After the completion of stirring, the solvent is removed, and the residue is dried and pulverized to obtain the desired treated powder.

For the solvent, ones in which various hydrophobizing agents and cationic surfactants can be dissolved, such as methyl alcohol, ethyl alcohol, and isopropyl alcohol, may be used, and isopropyl alcohol is particularly preferred.

The treated titanium dioxide powder wherein silica-coated titanium dioxide is hydrophobized with a silane coupling agent and a cationic surfactant (a1) can be prepared in the above-mentioned method. Examples of commercially available ones include, for example, titanium dioxide OTQ-MT-100Si manufactured by Tayca Corporation. The treated powder of the present invention can be also prepared by treating a silane coupling agent-treated powder, which is commercially available, with a cationic surfactant.

In the titanium dioxide dispersion of the present invention, the amount of treated titanium dioxide powder (a) is 25 to 60% by mass and more preferably 35 to 50% by mass. When the amount of treated titanium dioxide powder (a) is less than 25% by mass, the primary object of the present invention (i.e., to obtain a dispersion which is good in a system having a high concentration of titanium dioxide powder) cannot be achieved. When it exceeds 60% by mass, it becomes difficult to obtain a stable dispersion.

The one or more oils (b) selected from isohexadecane, isododecane, 2-ethylhexyl 2-ethylhexanoate, isononyl isononate, 2-ethylhexyl isononanoate, isononyl 2-ethylhexanoate, and polypropylene glycol dipivalate can disperse the treated powder stably. When oils other than the above-mentioned oils are used, it may be difficult to obtain a stable dispersion.

Among them, isohexadecane, 2-ethylhexyl 2-ethylhexanoate, and polypropylene glycol dipivalate are particularly preferred. When any of these oils are used, a good dispersibility is maintained and the feeling in use is excellent even when other UV absorbers are added to. Furthermore, among these oils, polypropylene glycol dipivalate is even more preferred because it provides a light fresh feeling and can be easily mixed with UV absorbers.

Examples of polypropylene glycol dipivalate include, for example, tripropylene glycol dipivalate described in WO2003/26698.

In the present invention, the total amount of oils (b) is 40 to 75% by mass with respect to the whole titanium dioxide dispersion and preferably 50 to 65% by mass.

The siloxane compound (c) represented by the following formula (1) used in the present invention is used as a dispersant.

$$R^1_a R^2_b R^3_c SiO_{(4-a-b-c)/2} \quad (1)$$

Specific examples of Ws include alkyl groups such as methyl, ethyl, propyl, butyl, pentyl, hexyl, heptyl, octyl, nonyl, decyl, undecyl, dodecyl, tridecyl, tetradecyl, hexadecyl, octadecyl, and eicosyl groups; cycloalkyl groups such as cyclopentyl and cyclohexyl groups; aryl groups such as phenyl and tolyl groups; aralkyl groups such as benzyl and phenethyl groups; fluorine-substituted alkyl groups such as trifluoropropyl and heptadecafluorodecyl groups; amino-substituted alkyl groups such as 3-aminopropyl and 3-[(2-aminoethyl)amino]propyl groups; and carboxy-substituted alkyl groups such as 3-carboxypropyl group. It is necessary that a part of $R^1$s are at least one or more alkyl groups having 10 or more carbon atoms, and specifically they are long-chain alkyl groups such as decyl, undecyl, dodecyl, tridecyl, tetradecyl, hexadecyl, octadecyl, and eicosyl groups.

A part of $R^1$s may be organic groups represented by the following formula (2). In the formula, $R^4$ is a hydrocarbon group having 4 to 30 carbon atoms or an organic group represented by $R^6$—(CO)— wherein $R^6$ is a hydrocarbon group having 1 to 30 carbon atoms. m is any integer of $0 \leq m \leq 15$, and d and e are respectively any integer of $0 \leq d \leq 50$ and $0 \leq e \leq 50$.

$$—C_m H_{2m}—O—(C_2H_4O)_d(C_3H_6O)_e—R^4 \quad (2)$$

The part of this $R^1$s are alcohol residues or alkenyl-added residues, and specific examples include —O—$(C_2H_4O)_d$$(C_3H_6O)_e$—$R^4$ when m=0.

In this case, when d=0 and e=0, examples of $R^1$s include alkoxy groups having 4 to 30 carbon atoms such as lower alkoxy groups (e.g., a butoxy group) and higher alkoxy groups (e.g., an oleyloxy group such as cetyl alcohol, oleyl alcohol, and stearyl alcohol, and a stearoxy group); and fatty acid residues (e.g., acetic acid, lactic acid, butyric acid, oleic acid, stearic acid, and behenic acid). When d>1 and e>1, examples of Ws include alcohol residues of an alkylene oxide adduct of a higher alcohol (wherein the terminal is a hydroxyl group).

When m≥1 and d=e=0, m is preferably 3, 5, or 11 in particular. In such case, $R^1$ is allyl ether residue, pentenyl ether residue, or undecenyl ether residue, and examples of $R^1$s include allyl stearyl ether residue, pentenyl behenyl ether residue, and undecenyl oleyl ether residue depending on the substituent of $R^4$. When d or e is not 0, there exists an alkoxy or ester group via polyoxyalkylene. In this context, regardless of the integers of d and e, the hydrolysis resistance may be poor when m=0, and the odor of oil is strong when d is 15 or more. Thus, it is desirable that m is 3 to 5.

$R^2$s are identical or different organic groups selected from an organic group having a polyoxyalkylene group represented by the following formula (3) or an organic group represented by the following formula (4).

$$—C_m H_{2m}—O—(C_2H_4O)_f(C_3H_6O)_g—R^5 \quad (3)$$

$$-Q-O—X \quad (4)$$

(In the formula (4), Q represents a divalent hydrocarbon group having 3 to 20 carbon atoms which may contain at least one of an ether bond and an ester bond, and X represents a polyhydric alcohol-substituted hydrocarbon group having at least two hydroxyl groups.)

$R^5$ in the formula (3) is a hydrogen atom, a hydrocarbon group having 1 to 30 carbon atoms, or an organic group represented by $R^6$—(CO)— wherein $R^6$ is a hydrocarbon group having 1 to 30 carbon atoms. f is an integer of 2 to 200 and preferably 5 to 100, g is an integer of 0 to 200 and preferably 0 to 100, and f+g is 3 to 200 and preferably 5 to 100. To provide enough hydrophilicity to obtain a water-in-oil emulsion, f/g≥1 is preferred. When the polyoxyalkylene group represented by the formula (3) includes both of an ethylene oxide unit and a propylene oxide unit, it may be a block or random polymer of both units.

Examples of Q in the formula (4) include —$(CH_2)_2$—, —$(CH_2)_3$—, —$CH_2CH(CH_3)CH_2$—, —$(CH_2)_4$—, —$(CH_2)_6$—, —$(CH_2)_7$—, —$(CH_2)_8$—, —$(CH_2)_2$—CH($CH_2CH_2CH_3$)—, —$CH_2$—CH($CH_2CH_3$)—, —$(CH_2)_3$—O—$(CH_2)_2$—, —$(CH_2)_3$—O—$(CH_2)_2$—O—$(CH_2)_2$—, —$(CH_2)_3$—O—$CH_2CH(CH_3)$—, and —$CH_2CH(CH_3)$—$COO(CH_2)_2$—. X is a polyhydric alcohol-substituted hydrocarbon group having at least two hydroxyl groups, and it is preferably a hydrocarbon group selected from glycerin derivatives.

Examples of glycerin derivatives include the compounds represented by the following formulas (A) to (C).

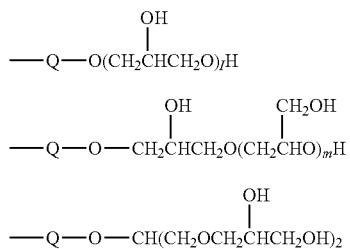

Qs in the above-mentioned formulas (A) to (C) are identical to Q in the formula (3), and 1 and m are respectively any integer of 1 to 20. A part of the hydroxy groups in the compounds may be substituted with an alkoxy or ester group.

$R^3$ is organopolysiloxane represented by the following formula (5). In the formula (5), h is an integer of 0 to 500 and preferably 1 to 50. n is an integer of 1 to 5, and n takes 2 in particular when the organopolysiloxane is synthesized by the reaction between vinyl group and hydrogen siloxane. When h exceeds 500, there may be problems such as a deteriorated reactivity with the hydrogen siloxane of main chain.

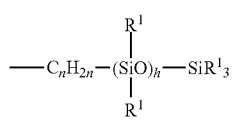

In the component (c) represented by the formula (1) in the present invention, a is any of 1.0 to 2.5 and preferably 1.2 to 2.3. When a is less than 1.0, the compatibility with oil agents becomes poor. When a is more than 2.5, the hydrophilicity becomes poor. b is any of 0.001 to 1.5 and preferably 0.05 to 1.0. When b is less than 0.001, the hydrophilicity becomes poor. When b is more than 1.5, the hydrophilicity becomes too high. c is any of 0.001 to 1.5 and preferably 0.05 to 1.0. When c is less than 0.001, the compatibility with silicone oil becomes poor. When c is more than 1.5, the hydrophilicity becomes poor.

The weight average molecular weight of the component (c) represented by the formula (1) used in the present invention is not limited in particular, and it is preferably 500 to 200000 and more preferably 1000 to 100000.

Examples of commercially available products for the component (c) in the present invention include KF-6038 (manufactured by Shin-Etsu Chemical Co., Ltd., labeling name: lauryl PEG-9 polydimethylsiloxyethyl dimethicone) and KF-6105 (manufactured by Shin-Etsu Chemical Co., Ltd., labeling name: lauryl polyglyceryl-3 polydimethylsiloxyethyl dimethicone) which are polyoxyalkylene/alkyl comodified organopolysiloxanes. The component (c) particularly preferred in the present invention is the one in which $R^2$ has the structure represented by the formula (3), which is lauryl PEG-9 polydimethylsiloxyethyl dimethicone.

In the present invention, the amount of component (c) is 3 to 10% by mass with respect to the whole titanium dioxide dispersion and preferably 3 to 5% by mass.

The titanium dioxide dispersion of the present invention can be obtained by adding the treated titanium dioxide powder (a) and the polyoxyalkylene/alkyl comodified organopolysiloxane (c) to the oils (b) and dispersing the mixture with a disperser. For dispersing, a disperser having a strong dispersion ability, such as a paint shaker, a sand mill, a roller mill, a bead mill, and a high-pressure homogenizer, is suitably selected for use. Among them, a media agitating mill having a high dispersion ability such as a bead mill is preferably used.

The cosmetic of the present invention is produced by incorporating the above-mentioned titanium dioxide dispersion, and the treated titanium dioxide powder (a) is incorporated for the purposes of UV protection and so on. The amount of titanium dioxide dispersion in the cosmetic cannot be flatly specified because it varies depending on product forms of the cosmetic and the amount of other components having more specific purposes. However, generally, it is preferably 5 to 30% by mass in the whole cosmetic, and in particular 7 to 20% by mass. When the amount of titanium dioxide dispersion is less than 5% by mass, a sufficient effect of UV protection may not be achieved. When it exceeds 30% by mass, the usability and the stability may be deteriorated.

In the cosmetic of the present invention, as necessary, other components generally used in cosmetics, pharmaceuticals, and so on can be arbitrarily incorporated in addition to the above-mentioned titanium dioxide dispersion as long as the effect of the present invention is not deteriorated. Examples of such components include other powders, other liquid oils, solid oils, waxes, hydrocarbons, higher alcohols, esters, silicones, anionic surfactants, cationic surfactants, amphoteric surfactants, nonionic surfactants, moisturizers, water-soluble polymers, thickeners, coating agents, UV absorbers, metal ion sequestering agents, lower alcohols, polyhydric alcohols, saccharides, amino acids, organic amines, polymer emulsions, pH adjusters, skin nutrients, vitamins, antioxidants, antioxidant aids, perfumes, and water. The cosmetic of the present invention can be produced by a normal production method depending on desired product form.

The cosmetic of the present invention can be widely used in cosmetic products, pharmaceuticals, and quasi-drugs, which are applied to external skin. The cosmetic can be provided in any product forms such as solution, solubilized, emulsified, powder-dispersed, water-oil 2-layered, water-oil-powder 3-layered, gel, aerosol, mist, and capsule forms.

In case of oil-in-water emulsion cosmetics, even when a titanium dioxide dispersion maintains a good dispersion state, the incorporation into a cosmetic preparation often leads to a deteriorated emulsion stability or powder agglomerations. However, since the titanium dioxide dispersion of the present invention has a good emulsion stability even in an oil-in-water emulsion cosmetic and hardly causes powder agglomerations, the product form is preferably an oil-in-water emulsion cosmetic in particular.

The cosmetic of the present invention can be provided in any products, which are not limited in particular, and the examples include makeup cosmetics such as foundation, face powder, lipstick, eye shadow, cheek, mascara, and eyeliner; base creams; and hair creams. The product is preferably a sunscreen cosmetic.

It is preferred that the cosmetic according to the present invention further contains organic UV absorbers.

Examples of the UV absorbers include benzoic acid UV absorbers such as p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid UV absorbers such as homomethyl N-acetylanthranilate; salicylic acid UV absorbers such as amyl salicylate, menthyl salicylate, homomethyl salicylate, octyl salicylate, phenyl salicylate, benzyl salicylate, and p-isopropanolphenyl salicylate; cinnamic acid UV absorbers such as octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl-diparamethoxy cinnamate; benzophenone UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol; 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; and dimorpholinopyridazinone.

As the dispersion medium used in the titanium dioxide dispersion of the present invention has an excellent compatibility especially with oil-soluble UV absorbers, the problems such as the precipitation of UV absorbers hardly occur even during a long-term preservation, thus a stable cosmetic can be obtained. Even when UV absorbers which are hardly soluble in silicone oils, such as diethylamino hydroxybenzoyl hexyl benzoate (e.g., product name: Uvinul A Plus, manufactured by BASF Corporation), ethylhexyl triazine (e.g., product name: Uvinul T-150, manufactured by BASF Corporation), t-butyl methoxydibenzoylmethane (e.g., product name: Parsol 1789, manufactured by DSM), bis-ethylhexyloxyphenol methoxyphenyl triazine (e.g., product name: Tinosorb S, manufactured by Ciba Inc.), diethylhexyl butamido triazone (e.g., product name: Uvasorb HEB, manufactured by 3V sigma), and oxybenzone-3 (e.g., product name: Uvinul M-40, manufactured by BASF Corporation), are incorporated, the problems such as the precipitation of UV absorbers hardly occur, thus the stability of the cosmetic preparation is excellent.

EXAMPLES

Hereinafter, the present invention will be further described in details in the following examples. However, it is to be understood that these examples should not limit the present invention. Unless otherwise noted, the amount is represented as % by mass.

The method for testing effects used in the present invention is explained prior to the explanation of the examples.

(1) Evaluation Test for Dispersibility

Glass beads (1 mm) are added to oils and treated titanium dioxide powders so that the weight ratio of the oils to the treated titanium dioxide powder in the titanium dioxide dispersion is 1:1, and the mixture is mixed with a paint shaker for 1 hour to prepare a slurry dispersion.

(Observation of Dispersion State)

The state of film of each dispersion film is visually observed and evaluated in accordance with the following criteria.

◯: The film is homogenous, transparent, and palish.

◯Δ: The film is slightly homogenous, translucent, and palish.

Δ: The film is slightly inhomogeneous, opaque, and white. Aggregates can be partly observed.

ΔX: The film is quite inhomogeneous, opaque, and white. Aggregates can be observed.

X: The film is thoroughly inhomogeneous, opaque, and white. There are a lot of aggregates.

Test Example 1

35% by mass of each of the various treated titanium dioxide powders shown in Table 1, 5% by mass of dispersant (KF-6038, manufactured by Shin-Etsu Chemical Co., Ltd.), and 60% by mass of oils shown in Table 1 were mixed to prepare a titanium dioxide dispersion, and its dispersibility was evaluated in the above-mentioned method. The result is shown in Table 1.

The details of the titanium dioxides (surface treating agents and hydrophobizing treating agents) in Table 1 are as shown in Table 2.

TABLE 1

| Treated titanium dioxide powder | Cyclic silicone (pentamer) | Dimethicone (6cs) | Phenyl trimethicone | Isohexadecane | Polydecene | 2-EH 2-ethylhexanoate | Trioctanoin | PBG/ PPG-9/1 copolymer | PPG-3 dipivalate | PEG/ PPG14/ 7DME |
|---|---|---|---|---|---|---|---|---|---|---|
| OTQ-MT-100Si | ◯ | X | X | ◯ | X | ◯ | Δ | X | ◯ | X |
| E730-1 | ◯ | Δ | ◯Δ | ◯ | ◯ | ◯ | X | X | ◯ | X |
| Titanium dioxide TTO-S-4 | ◯ | X | X | ◯ | X | ◯ | X | X | ◯ | X |
| TS complex | ◯ | Δ | ◯Δ | ◯ | Δ | ◯ | Δ | X | ◯ | X |

TABLE 2

| Titanium dioxide | Surface treating agent | Hydrophobizing treating agent |
|---|---|---|
| OTQ-MT-100Si | Silica | Octyltriethoxysilane Cation DSV (dimethyl distearyl ammonium chloride) |
| E730-1 | Silica | Octyltriethoxysilane |
| Titanium dioxide TTO-S-4 | Alumina | Stearic acid |

TABLE 2-continued

| Titanium dioxide | Surface treating agent | Hydrophobizing treating agent |
|---|---|---|
| TS complex | Alumina | Stearic acid |
| | Silica | Hexyl silane |

From Table 1, it can be understood that cyclic silicone, isohexadecan, 2-ethylhexyl 2-ethylhexanoate (2-EH 2-ethylhexanoate), and polypropylene glycol dipivalate show better dispersibility in various treated titanium dioxide powders, compared with the other organic solvents. In this context, Silicone KF56 (manufactured by Shin-Etsu Chemical Co., Ltd.) is used as phenyl trimethicone, a copolymer of polybutylene glycol and polypropylene glycol having the average mol ratio of 9:1 is used as PBG/PPG-9/1 copolymer, PEG/PPG14/7DME is a random polymer, wherein the mol ratio of ethylene oxide to propylene oxide is 14:7 and terminals are sequestered with methyl groups.

Examples 1 to 9

Comparative Examples 1 to 3

An oil-in-water sunscreen cosmetic was prepared with each formulation shown in the following Tables 3 and 4, and the emulsion state and the stability in low temperature was evaluated in the following method. Also, the dispersibility of each of the titanium dioxide dispersions used in Examples and Comparative Examples was evaluated in the method as described above.

In this context, the percentage of the components in each titanium dioxide dispersion was 50% by mass of oils, 45% by mass of powder, and 5% by mass of dispersant (KF-6038, manufactured by Shin-Etsu Chemical Co., Ltd.).

(Observation of Emulsion State)

The emulsion state of each cosmetic was evaluated in accordance with the following criteria.

⊚: The emulsion particles are very fine (1 to 2.5 μm) and homogenous, and no separation is observed.

O: The emulsion particles are fine (1 to 5 μm) and homogenous, and no separation is observed.

Δ: The emulsion particles are fine (1 to 5 μm) and homogenous, and the oils are slightly separated in the upper portion.

X: The emulsion particles are coarse (1 to 20 μm) and inhomogenous, and the oils are apparently separated in the upper portion.

(Observation for Stability in Low Temperature)

After each cosmetic was preserved at −20° C. for one month, it was evaluated with the following criteria.

O: Abnormality is not observed in the appearance, and it is not observed even under polarized light using a microscope.

X: Crystals derived from UV absorbers are observed in the appearance, and the apparent reflected lights are observed under polarized light.

TABLE 3

| | | Ex. 1 | Ex. 2 | Ex. 3 | Ex. 4 | Ex. 5 | Ex. 6 |
|---|---|---|---|---|---|---|---|
| Water | Ion-exchanged water | Balance | Balance | Balance | Balance | Balance | Balance |
| Moisturizer | Glycerin | 1 | 1 | 1 | 1 | 1 | 1 |
| Surfactant | PEG/PPG-50/40 dimethyl ether | 0.5 | 0.5 | 0.5 | 0.5 | 0.5 | 0.5 |
| | Polyoxyethylene sorbitan monostearate (20EO) *1 | 0.5 | 0.5 | 0.5 | 0.5 | 0.5 | 0.5 |
| Thickner | Acrylic acid/alkyl acrylate (C10-30) copolymer *2 | 0.1 | 0.1 | 0.1 | 0.1 | 0.1 | 0.1 |
| | Carboxyvinyl polymer | 0.2 | 0.2 | 0.2 | 0.2 | 0.2 | 0.2 |
| Titanium dioxide dispersion | OTQ-MT-100Si (2-ethylhexyl 2-ethylhexanoate-KF6038 solution) | 15 | — | — | — | — | — |
| | E730-1 (2-ethylhexyl 2-ethylhexanoate-KF6038 solution) | — | 15 | — | — | — | — |
| | Titanium dioxide TTO-S-4 (2-ethylhexyl 2-ethylhexanoate-KF6038 solution) | — | — | 15 | — | — | — |
| | TS complex (2-ethylhexyl 2-ethylhexanoate-KF6038 solution) | — | — | — | 15 | — | — |
| | OTQ-MT-100Si (isohexadecane-KF6038 solution) | — | — | — | — | 15 | — |
| | OTQ-MT-100Si (isododecane-KF6038 solution) | — | — | — | — | — | 15 |
| | OTQ-MT-100Si (isononyl 2-ethylhexanoate-KF6038 solution) | — | — | — | — | — | — |
| | OTQ-MT-100Si (2-ethylhexyl isononanoate-KF6038 solution) | — | — | — | — | — | — |
| | OTQ-MT-100Si (polypropylene glycol dipivalate-KF6038 solution) | — | — | — | — | — | — |
| | OTQ-MT-100Si (cyclic silicone pentamer-KF6038 solution) | — | — | — | — | — | — |
| | OTQ-MT-100Si (trioctanoin-KF6038 solution) | — | — | — | — | — | — |
| | E730-1 (polydecene-KF6038 solution) | — | — | — | — | — | — |
| Oil | Decamethylcyclopentasiloxane | 2 | 2 | 2 | 2 | 2 | 2 |
| | Dimethicone | 4 | 4 | 4 | 4 | 4 | 4 |
| | Caprylyl methicone | 5 | 5 | 5 | 5 | 5 | 5 |
| | Phenyl trimethicone *3 | 3 | 3 | 3 | 3 | 3 | 3 |
| | 2-Ethylhexyl 2-ethylhexanoate | 2 | 2 | 2 | 2 | 2 | 2 |
| UV absorber | Octyl methoxycinnamate | 5 | 5 | 5 | 5 | 5 | 5 |
| | Diethylamino hydroxybenzoyl hexyl benzoate *4 | 1 | 1 | 1 | 1 | 1 | 1 |
| Powder | Spherical silica | 1 | 1 | 1 | 1 | 1 | 1 |
| Buffer | Citric acid | Q.S. | Q.S. | Q.S. | Q.S. | Q.S. | Q.S. |
| | Sodium citrate | Q.S. | Q.S. | Q.S. | Q.S. | Q.S. | Q.S. |

TABLE 3-continued

|  |  | Ex. 1 | Ex. 2 | Ex. 3 | Ex. 4 | Ex. 5 | Ex. 6 |
|---|---|---|---|---|---|---|---|
| Chelating agent | Edetate | Q.S. | Q.S. | Q.S. | Q.S. | Q.S. | Q.S. |
| Perfume | Perfume | Q.S. | Q.S. | Q.S. | Q.S. | Q.S. | Q.S. |
|  | Dispersibility | ○ | ○ | ○ | ○ | ○ | ○ |
|  | Emulsion state | ⊚ | ○ | ○ | ○ | ○ | ○ |
| Precipitation of diethylamino hydroxybenzoyl hexyl benzoate (−20° C., after one month) | | ○ | ○ | ○ | ○ | ○ | ○ |

TABLE 4

|  |  | Ex. 7 | Ex. 8 | Ex. 9 | Comp. Ex. 1 | Comp. Ex. 2 | Comp. Ex. 3 |
|---|---|---|---|---|---|---|---|
| Water | Ion-exchanged water | Balance | Balance | Balance | Balance | Balance | Balance |
| Moisturizer | Glycerin | 1 | 1 | 1 | 1 | 1 | 1 |
| Surfactant | PEG/PPG-50/40 dimethyl ether | 0.5 | 0.5 | 0.5 | 0.5 | 0.5 | 0.5 |
|  | Polyoxyethylene sorbitan monostearate (20EO) *1 | 0.5 | 0.5 | 0.5 | 0.5 | 0.5 | 0.5 |
| Thickner | Acrylic acid/Alkyl acrylate (C10-30) copolymer *2 | 0.1 | 0.1 | 0.1 | 0.1 | 0.1 | 0.1 |
|  | Carboxyvinyl polymer | 0.2 | 0.2 | 0.2 | 0.2 | 0.2 | 0.2 |
| Titanium dioxide dispersion | OTQ-MT-100Si (2-ethylhexyl 2-ethylhexanoate-KF6038 solution) | — | — | — | — | — | — |
|  | E730-1 (2-ethylhexyl 2-ethylhexanoate-KF6038 solution) | — | — | — | — | — | — |
|  | Titanium dioxide TTO-S-4 (2-ethylhexyl 2-ethylhexanoate-KF6038 solution) | — | — | — | — | — | — |
|  | TS complex (2-ethylhexyl 2-ethylhexanoate-KF6038 solution) | — | — | — | — | — | — |
|  | OTQ-MT-100Si (isohexadecane-KF6038 solution) | — | — | — | — | — | — |
|  | OTQ-MT-100Si (isododecane-KF6038 solution) | — | — | — | — | — | — |
|  | OTQ-MT-100Si (isononyl 2-ethylhexanoate-KF6038 solution) | 15 | — | — | — | — | — |
|  | OTQ-MT-100Si (2-ethylhexyl isononanoate-KF6038 solution) | — | 15 | — | — | — | — |
|  | OTQ-MT-100Si (polypropylene glycol dipivalate-KF6038 solution) | — | — | 15 | — | — | — |
|  | OTQ-MT-100Si (cyclic silicone pentamer-KF6038 solution) | — | — | — | 15 | — | — |
|  | OTQ-MT-100Si (trioctanoin-KF6038 solution) | — | — | — | — | 15 | — |
|  | E730-1 (polydecene-KF6038 solution) | — | — | — | — | — | 15 |
| Oil | Decamethylcyclopentasiloxane | 2 | 2 | 2 | 2 | 2 | 2 |
|  | Dimethicone | 4 | 4 | 4 | 4 | 4 | 4 |
|  | Caprylyl methicone | 5 | 5 | 5 | 5 | 5 | 5 |
|  | Phenyl trimethicone *3 | 3 | 3 | 3 | 3 | 3 | 3 |
|  | 2-Ethylhexyl 2-ethylhexanoate | 2 | 2 | 2 | 2 | 2 | 2 |
| UV absorber | Octyl methoxycinnamate | 5 | 5 | 5 | 5 | 5 | 5 |
|  | Diethylamino hydroxybenzoyl hexyl benzoate | 1 | 1 | 1 | 1 | 1 | 1 |
| Powder | Spherical silica | 1 | 1 | 1 | 1 | 1 | 1 |
| Buffer | Citric acid | Q.S. | Q.S. | Q.S. | Q.S. | Q.S. | Q.S. |
|  | Sodium citrate | Q.S. | Q.S. | Q.S. | Q.S. | Q.S. | Q.S. |
| Chelating agent | Edetate | Q.S. | Q.S. | Q.S. | Q.S. | Q.S. | Q.S. |
| Perfume | Perfume | Q.S. | Q.S. | Q.S. | Q.S. | Q.S. | Q.S. |
|  | Dispersibility | ○ | ○ | ○ | ○ | Δ | ○ |
|  | Emulsion state | ○ | ○ | ⊚ | ○ | X | X |
| Precipitation of diethylamino hydroxybenzoyl hexyl benzoate (−20° C., after one month) | | ○ | ○ | ○ | X | ○ | ○ |

*1: Nikkol TS-10 V (manufactured by Nikko Chemicals Co., Ltd.)
*2: Pemulen TR-2 (manufactured by Goodrich)
*3: Silicone KF-56 (manufactured by Shin-Etsu Chemical Co., Ltd.)
*4: Uvinul A Plus (manufactured by BASF Corporation)

From Tables 3 and 4, it can be understood that each cosmetic in which the titanium dioxide dispersion of the present invention is incorporated is excellent with preparations as it is well emulsified and has no powder agglomeration. Especially, the cosmetic incorporating 2-ethylhexyl 2-ethylhexanoate dispersion of the powder which is hydrophobized with octyltriethoxysilane and dimethyl distearyl ammonium chloride (Example 1) and the cosmetic incorporating polypropylene glycol dipivalate dispersion of the powder which is hydrophobized with octyltriethoxysilane and dimethyl distearyl ammonium chloride (Example 9) have excellent emulsion states in particular.

On the other hand, when cyclic silicone pentamer, trioctanoin, or polydecene was used as a dispersion medium for the titanium dioxide, the dispersion has an excellent dispersion state. However, when it was incorporated in cosmetic, the emulsion state became unstable, and the oil- and poorly-soluble UV absorbers precipitated during the preservation. Thus, a stable cosmetic could not be obtained (Comparative Examples 1 to 3).

Hereinafter, the formulation examples of the cosmetics using the titanium dioxide dispersion of the present invention will be described. However, the present invention is not limited by these formulation examples, and it is specified by the scope of claims.

Formulation Example 1

Milky Lotion (1) Decamethylcyclopentasiloxane 3% by mass
(2) Phenyl trimethicone 3
(3) Behenyl alcohol 1
(4) Titanium dioxide dispersion (OTQ-MT-100Si-polypropylene glycol dipivalate-KF6038) 15
(5) Polyoxyethylene glyceryl isostearate 1.5
(6) Polyoxyethylene glyceryl monostearate 1
(7) bis-Ethylhexyloxyphenol methoxyphenyl triazine (Tinosorb S) 2
(8) t-Butyl methoxydibenzoylmethane (Parsol 1789) 2
(9) Octyl methoxycinnamate 5.5
(10) Octocrylene 5
(11) Purified water Balance
(12) Carboxyvinyl polymer 0.3
(13) Alkyl-modified carboxyvinyl polymer 0.1
(14) Potassium hydroxide Q.S.
(15) 1,3-Butylene glycol 5
(16) Tranexamic acid 2
(17) Trisodium edetate Q.S.
(18) Xanthan gum Q.S.
(19) Phenoxyethanol Q.S.
  (Production Method)
  The oil phase of (1) to (10) was heated to 80° C. and uniformly dissolved.
  (12) and (13) were uniformly dissolved in (11), and the mixture was neutralized with (14).
  (15) to (19) were added to the portion of (11) to (14), which has been prepared in the foregoing step, and uniformly mixed.
  The oil phase of (1) to (10) was added to the aqueous phase of (11) to (19), and the mixture was uniformly emulsified with a shearing machine such as a homogenizer to obtain the desired product.

Formulation Example 2

Cream (1) Stearic acid 1% by mass
(2) Palmitic acid 0.5
(3) Behenic acid 1
(4) Diethylamino hydroxybenzoyl hexyl benzoate (Uvinul A Plus, manufactured by BASF Corporation) 2
(5) Ethylhexyl triazine (Uvinul T-150, manufactured by BASF Corporation) 1
(6) Titanium dioxide dispersion (TS complex-(2-ethylhexyl 2-ethylhexanoate)-KF6038) 20
(7) Cetyl 2-ethylhexanoate 4
(8) Octyl methoxycinnamate 5.5
(9) Octocrylene 5
(10) Polyoxyethylene glyceryl isostearate 1
(11) Glyceryl monostearate 1
(12) Polyoxyethylene glyceryl monostearate 1
(13) Eicosene/vinylpyrrolidone copolymer 2
(14) Purified water Balance
(15) Dipropylene glycol 5
(16) 1,3-Butanediol 5
(17) Phenoxyethanol Q.S.
(18) Trisodium edetate Q.S.
(19) Bentonite 1
(20) Triethanolamine Q.S.
  (Production Method)
  The oil phase of (1) to (13) was heated to 70° C. and uniformly dissolved.
  (14) to (18) were uniformly dissolved, then (19) was dispersed therein, and the mixture was heated to 70° C.
  The oil phase of (1) to (13) was added to the aqueous phase of (14) to (19), and the mixture was neutralized with (20). Then, it was uniformly emulsified with a shearing machine such as a homogenizer and cooled to room temperature by stirring to obtain the desired product.

Formulation Example 3

Milky Lotion (1) Phenyl trimethicone 1% by mass
(2) Polydecene 2
(3) Diisopropyl sebacate 3
(4) Dioctyl succinate 2
(5) Diethylhexyl butamide triazone (Uvasorb HEB, manufactured by 3V sigma) 3
(6) Oxybenzone-3 (Uvinul M-40, manufactured by BASF Corporation) 2
(7) Titanium dioxide dispersion (TTO-S-4-isohexadecane-KF6105) 20
(8) Cetyl 2-ethylhexanoate 1
(9) Octyl methoxycinnamate 5
(10) Octocrylene 4
(11) Polyoxyethylene glyceryl monoisostearate (EO60) 1
(12) Glyceryl monostearate (EO5) 1
(13) Purified water Balance
(14) Dipropylene glycol 5
(15) 1,3-Butanediol 5
(16) Phenoxyethanol Q.S.
(17) Trisodium edetate Q.S.
  (Production Method)
  The oil phase of (1) to (12) was heated to 70° C. and uniformly dissolved.
  The water phase of (13) to (17) were uniformly dissolved, the heated oil phase of (1) to (12) was added thereto, and the mixture was emulsified. Then, it was uniformly emulsified with a shearing machine such as a homogenizer to obtain the desired product.

What is claimed is:
1. A titanium dioxide dispersion consisting essentially of following (a) to (c):
  (a) a hydrophobized, silica- or alumina-coated titanium dioxide powder;
  (b) one or two oils selected from isohexadecane and isododecane; and
  (c) a siloxane compound represented by following formula (1):

$$R^1_a R^2_b R^3_c SiO_{(4-a-b-c)/2} \qquad (1)$$

wherein $R^1$s are identical or different organic groups in which at least one or more alkyl groups having 10 or more carbon atoms are contained as essential components, and $R^1$s are selected from the organic groups having 1 to 18 carbon atoms such as an alkyl group, an aryl group, an aralkyl group, a fluorine-substituted alkyl group, an amino-substituted alkyl group, a carboxy-substituted alkyl group, and an organic group represented by following formula (2):

$$—C_mH_{2m}—O—(C_2H_4O)_d(C_3H_6O)_o—R^4 \quad (2)$$

$R^2$s are identical or different organic groups selected from an organic group having a polyoxyalkylene group represented by following formula (3) and an organic group represented by following formula (4) wherein Q represents a divalent hydrocarbon group having 3 to 20 carbon atoms which may have at least one of an ether bond and an ester bond, and X represents a polyhydric alcohol-substituted hydrocarbon group having at least two hydroxyl groups;

$$—C_mH_{2m}—O—(C_2H_4O)_f(C_3H_6O)_g—R^5 \quad (3)$$

$$\text{-Q-O—X} \quad (4)$$

$R^3$ is organopolysiloxane represented by following formula (5); $R^4$ is a hydrocarbon group having 4 to 30 carbon atoms or an organic group represented by $R^6$—(CO)—; $R^5$ is a hydrogen atom, a hydrocarbon group having 1 to 30 carbon atoms, or an organic group represented by $R^6$—(CO)—; $R^6$ is a hydrocarbon group having 1 to 30 carbon atoms;

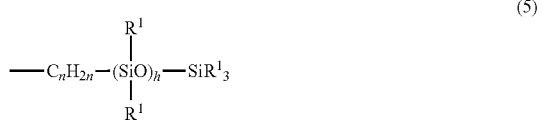

$$——C_nH_{2n}—(SiO)_h—SiR^1_3 \quad (5)$$

d and e are respectively any integer of $0 \le d \le 50$ and $0 \le e \le 50$; f and g are respectively any integer of $2 \le f \le 200$ and $0 \le g \le 200$, and f+g is 3 to 200; h is any integer of $1 \le h \le 500$; m and n are respectively any integer of $0 \le m \le 15$ and $1 \le n \le 5$; and a, b, and c are respectively any integer of $1.0 \le a \le 2.5$, $0.001 \le b \le 1.5$, and $0.001 \le c \le 1.5$.

2. The titanium dioxide dispersion according to claim 1, wherein the coated titanium dioxide powder (a) is powder in which the silica-coated titanium dioxide is treated with a silane coupling agent and a cationic surfactant.

3. The titanium dioxide dispersion according to claim 1, wherein amount of the coated titanium dioxide powder (a) is 25 to 60% by mass.

4. The titanium dioxide dispersion according to claim 1, wherein amount of the siloxane compound (c) is 3 to 10% by mass.

5. A cosmetic comprising the titanium dioxide dispersion according to claim 1.

6. The cosmetic according to claim 5, which is an oil-in-water emulsion cosmetic.

7. The cosmetic according to claim 5, further comprising one or more oil-soluble UV absorbers selected from diethylamino hydroxybenzoyl hexyl benzoate, ethylhexyl triazine, t-butyl methoxydibenzoylmethane, bis-ethylhexyloxyphenol methoxyphenyl triazine, diethylhexyl butamide triazone, and oxybenzone-3.

8. A cosmetic comprising the titanium dioxide dispersion according to claim 2.

9. The cosmetic according to claim 8, which is an oil-in-water emulsion cosmetic.

10. The cosmetic according to claim 8, further comprising one or more oil-soluble UV absorbers selected from diethylamino hydroxybenzoyl hexyl benzoate, ethylhexyl triazine, t-butyl methoxydibenzoylmethane, bis-ethylhexyloxyphenol methoxyphenyl triazine, diethylhexyl butamide triazone, and oxybenzone-3.

11. A cosmetic comprising the titanium dioxide dispersion according to claim 3.

12. The cosmetic according to claim 11, which is an oil-in-water emulsion cosmetic.

13. The cosmetic according to claim 11, further comprising one or more oil-soluble UV absorbers selected from diethylamino hydroxybenzoyl hexyl benzoate, ethylhexyl triazine, t-butyl methoxydibenzoylmethane, bis-ethylhexyloxyphenol methoxyphenyl triazine, diethylhexyl butamide triazone, and oxybenzone-3.

14. A cosmetic comprising the titanium dioxide dispersion according to claim 4.

15. The cosmetic according to claim 14, which is an oil-in-water emulsion cosmetic.

16. The cosmetic according to claim 14, further comprising one or more oil-soluble UV absorbers selected from diethylamino hydroxybenzoyl hexyl benzoate, ethylhexyl triazine, t-butyl methoxydibenzoylmethane, bis-ethylhexyloxyphenol methoxyphenyl triazine, diethylhexyl butamide triazone, and oxybenzone-3.

* * * * *